United States Patent [19]
Lambert et al.

[11] Patent Number: 5,840,859
[45] Date of Patent: Nov. 24, 1998

[54] (AMINOSTYRYL)PYRIDINIUM COMPOUNDS FOR RADIOLABELLING CELL MEMBRANES

[75] Inventors: Carol Lambert; Ronnie C. Mease, both of Fairfax, Va.; John G. McAfee, Chevy Chase, Md.

[73] Assignee: Research Corporation Technologies, Inc., Tucson, Ariz.

[21] Appl. No.: 673,798

[22] Filed: Jun. 27, 1996

Related U.S. Application Data

[60] Provisional application No. 60/000,903, Jul. 6, 1995.
[51] Int. Cl.$^6$ .......................... C09F 13/00; C07D 211/70; A61K 51/04
[52] U.S. Cl. .............................. 534/10; 534/14; 424/1.65; 424/1.85; 546/329; 546/334
[58] Field of Search .................................. 424/1.65, 1.85; 534/10, 14; 546/329, 334

[56] References Cited

U.S. PATENT DOCUMENTS

| | | | |
|---|---|---|---|
| 4,342,739 | 8/1982 | Kakimi et al. | 424/1 |
| 4,544,546 | 10/1985 | Wang et al. | 424/7.1 |
| 4,560,665 | 12/1985 | Nakae et al. | 436/172 |
| 4,636,479 | 1/1987 | Martin et al. | 436/533 |
| 4,698,263 | 10/1987 | Wagner et al. | 428/402.2 |
| 4,707,453 | 11/1987 | Wagner et al. | 436/501 |
| 5,021,571 | 6/1991 | Mease et al. | 544/166 |
| 5,089,663 | 2/1992 | Mease et al. | 562/507 |
| 5,292,938 | 3/1994 | Mease et al. | 562/507 |
| 5,334,729 | 8/1994 | Mease et al. | 548/546 |
| 5,369,036 | 11/1994 | Mercolino et al. | 436/523 |
| 5,385,822 | 1/1995 | Melnicoff et al. | 435/5 |

FOREIGN PATENT DOCUMENTS

| | | |
|---|---|---|
| 2129933 | 2/1995 | Canada . |
| WO 91/06011 | 5/1991 | WIPO . |

OTHER PUBLICATIONS

Lambert et al., *Nucl. Med. Biol.*, vol. 23(4), pp. 417–427, May 1996.

J. P. Corsetti, et al. "The Labeling of Lipoproteins for Studies of Cellular Binding with a Fluorescent Lipophilic Dye." *Anal.Biochem.* 195, pp. 122–128, (15 May 1991).

Otto A. Gansow. "Newer Approaches to the Radiolabeling of Monoclonal Antibodies by Use of Metal Chelates." *Nucl.Med.Biol.*, vol. 18, No. 4, pp. 369–381, (1991).

A. Hassner, et al. "Charge–Shift Probes of Membrane Potential. Synthesis", *J. Org. Chem.*, vol. 49, pp. 2546–2551, (1984).

E. Lannto. "Investigation of Suspected Intra–abdominal Sepsis: The Contribution of Nuclear Medicine." *Scandinavian Journal of Gastroenterology*, vol. 29,Suppl. 203, pp. 11–14, (1994).

Leslie M. Loew, et al. "Charge–Shift Probes of Membrane Potential." *Biophysical Journal*, vol.34, No.3, pp. 353–365, (Jun. 1981).

L. M. Loew, et al. "Charge–Shift Probes of Membrane Potential Characterisation of Aminostyrylpyridinium Dyes of the Squid Giant Axon." *ChemicalAbstracts,* 102, Abstract No. 128162w, p. 295, (1985).

J. G. McAfee, et al. "$^{99m}$Tc–HM–PAO for Leukocyte Labeling—Experimental Comparison with $^{111}$In Oxine in Dogs." *Eur.J.Nucl.Med.,*, vol.13, No.7, pp. 353–357, (1987).

A. M. Peters, et al. "Imaging Inflammation: Current Role of Labeled Autologous Leukocytes" *J. Nucl. Med.*, vol. 33, No. 1, pp. 65–67, (Jan. 1992).

S. H. Saverymuttu, et al. "Quantitative Fecal Indium 111–Labeled Leukocyte Excretion in the Assessment of Disease in Crohn's Disease." *Gastroent.*, vol.85, No.6, pp. 1333–1339, (1983).

Suresh C. Srivastava, et al. "Progress in Research in Ligands, Nuclides and Techniques for Labeling Monoclonal Antibodies." *Nuclear Medicine and Biology*, vol.18, No.6, pp. 589–603, (1991).

*Primary Examiner*—John Kight
*Assistant Examiner*—Lara C. Kelley
*Attorney, Agent, or Firm*—Schwegman, Lundberg, Woessner & Kluth, P.A.

[57] ABSTRACT

A compound is provided of formula I:

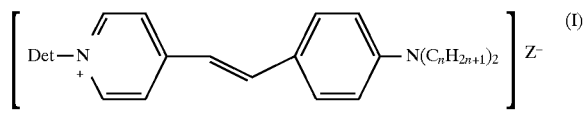

wherein n is 4–16, Det is an organic group comprising a radioisotope or capable of chelating a radioisotope, and $Z^-$ is one equivalent of a biologically acceptable anion, which compounds are useful to radiolabel cellular membranes, as of hematopoietic cells.

9 Claims, 3 Drawing Sheets

(AMINOSTYRYL)PYRIDINIUM COMPOUNDS FOR RADIOLABELLING CELL MEMBRANES

This invention was made with Government support under Contract No. CA-32853, awarded by the National Institutes of Health. The Government has certain rights in the invention.

This application claims the benefit of United States provisional application No. 60/000,903, filed Jul. 6, 1995. Furthermore, this application has small-entity status as per the verified statement claiming small-entity status of Small Business Concern filed concurrent with the provision application.

BACKGROUND OF THE INVENTION

Lipophilic fluorescent membrane permanent dyes have been used for over 15 years to measure membrane potential in both resting and activated neutrophils and lymphocytes in vitro. The lipophilic chelates $^{111}$In-oxine, $^{111}$-In-tropolone, and $^{99m}$Tc-HMPAO (hexamethylpropylene amine oxime) are used clinically to label mixed leukocytes for detection of focal inflammatory lesions. Leukocytes labeled in vitro with $^{99m}$Tc-HMPAO or the $^{111}$In-chelates are still the most widely accepted means of imaging inflammation. See, E. Lantto, Scand. J. Gastroent., 29 Supp, 203, 11 (1994). Because of improved image resolution, reduced radiation dose, low cost, and widespread clinical availability, $^{99m}$Tc-HMPAO is generally preferred for detecting acute abdominals sepsis, inflammatory bowel disease (IBD), soft tissue sepsis and osteomyelitis. This is in spite of the fact that $^{99m}$Tc-HMPAO is less stable both in vitro and in vivo than either of the $^{111}$In radiopharmaceuticals, and that with $^{99m}$Tc-HMPAO, there is diffuse abdominal radioactivity, gall bladder uptake, and renal excretion of an unidentified polar species containing $^{99m}$Tc as early as three hours post injection. Because of this $^{99m}$Tc leakage from labelled cells, $^{99m}$Tc-HMPAO is of no use in assessing urinary tract infections. In addition, $^{99m}$Tc-HMPAO leukocytes have lower absolute uptake in abscesses and lower target to background ratios than cells labeled with $^{111}$In-oxine. See, J. G. McAfee et al., Eur. J. Nucl. Med., 13,353 (1987).

In general, $^{111}$In-leukocytes are preferable for imaging chronic infection, renal sepsis, fevers of unknown origin, and intraabdominal abscesses in communication with the bowel lumen (A. M. Peters et al., J. Nucl. Med., 33, 65 (1992)). Quantification of whole body retention of radioactivity with $^{111}$In-labeled granulocytes and of fecal excretion of radioactivity with $^{111}$In-labeled neutrophils have been used as methods by which to quantify IBD and Crohn's Disease. S. H. Saverymuttu et al., Gastroent., 85, 1333 (1983). This quantification is not generally possible using $^{99m}$Tc-HMPAO unless early SPECT imaging is performed using the procedure of Weldon (Scand. J. Ent., 29 Supp 203, 61 (1994)).

To eliminate the leukocyte harvesting step required when $^{99m}$Tc-HMPAO or $^{111}$In-chelates are used for whole blood labeling, investigators have attempted a variety of directly injected in vivo agents for inflammation imaging. However, these techniques, which have employed labeled antibodies and liposomes, have serious drawbacks, including bone marrow uptake of the radiolabel, and low target tissue uptake.

Therefore, a need exists for improved agents to label mammalian cells, such as blood cells, associated with inflammation, infection, malignancies, and related pathologies.

SUMMARY OF THE INVENTION

The present invention provides compounds which can effectively radiolabel cellular membranes, methods of using them, and intermediates for the preparation thereof. Preferred compounds of the invention are (aminostyryl) pyridinium salts of formula (I):

wherein Det is an organic group comprising a detectable radioisotope, n is 4–16, preferably 6–10, and $Z^-$ is one equivalent of a biologically acceptable anion e.g., (I) is the pyridinium salt of an inorganic or organic acid which does not interfere with the ability of the compound of formula (I) to penetrate and label the membranes of target cells and is not toxic to the cells.

Preferably, Det is —CH$_2$—CH=CH—X wherein X is a radioisotope of iodine, i.e., $^{123}$I, $^{125}$I, or $^{131}$I; or Det is a chelating group comprising one equivalent of a metallic radioisotope such as $^{111}$In or $^{99m}$Tc, chelated by a polycarboxylic acid.

The compounds of formula (I) are preferably employed in vitro, in combination with a pharmaceutically acceptable carrier or vehicle, to label populations of mammalian cells, such as blood cells, including mixed leukocytes or lymphocytes. When introduced into a mammalian host, such as a human patient or animal, the labelled cells such as the leukocytes or lymphocytes, localize at a site of inflammation, infection, malignancy, or the like, thus enabling the imaging of said site, for diagnostic purposes or to enable the effective targeting of therapeutic agents.

Useful intermediates for the preparation of the compounds of formula (I) wherein Det is *I—CH=CH—CH$_2$— are compounds of formula (II):

wherein is 4–16, preferably 6–10, and $Z^-$ is one equivalent of a anion. Intermediates of formula (I) wherein Det is a chelating moiety which does not comprise a radiolabel, but which is capable of chelating a radioactive metal, also are an embodiment of the invention.

For example, compounds (I) and (II) are the pyridinium salts of an inorganic or organic acids, i.e., $Z^-$ is halide, sulfate, carbonate, phosphate, bicarbonate, acetate, citrate, tartarate, maleate, malate, propionate, and the like.

Using $^{125}$I- and $^{131}$I-labeled compounds of formula (I), canine mixed leukocytes and mononuclear cells were labeled in high yield (80–90%). Canine mixed leukocytes labeled with one compound of the invention, $^{125}$I- or $^{131}$I-4b, show a higher degree of localization in a sodium urate induced abscess in the dog model than do $^{111}$In-labeled mixed leukocytes.

Thus, the compounds of formula (I) can exhibit one or more of the following utilities:

a. Mixed leukocytes labeled with the radioiodinated compounds can be reinjected into the donor for the detection of either acute or chronic sites of inflammation/infection by diagnostic imaging techniques.

b. Autologous lymphocytes labeled with the radioiodinated compounds can be used for in vivo lymphocyte tracking and clinical imaging of lymphatic malignancies.

c. The present compounds can replace $^{111}$In-oxine as the preferred agent with which to label cultured lymphocytes for imaging metastatic melanoma prior to and after adoptive immunotherapy.

d. Any isolated cell population can be radiolabeled using the present compounds for in vitro testing or tracking in vivo.

e. Autologous lymphocytes labeled with the present compounds can be used to detect the lymphocytic infiltration of the pancreas which occurs prior to and during the early stages of Type I Diabetes Mellitus. Diagnostic imaging with the labeled lymphocytes could be used to assess the effectiveness of different drugs for treating Type I Diabetes during the early stages of the disease.

f. Autologous lymphocytes radiolabeled with the present compounds can be used to detect lymphocyte localization in transplanted organs as a means of early detection of the host's rejection of the transplanted tissue.

More specifically, mixed leukocytes labeled with $^{99m}$Tc-containing compounds of formula (I) can be used to image sites of acute inflammation. Nonspecific abdominal and renal uptake typical of $^{99m}$Tc-HNPAO should be reduced using $^{99m}$Tc chelated by a compound of formula (I). Mixed leukocytes labeled with [111]In-, [131]I-, or $^{123}$I-containing compounds of formula (I) can be used to image sites of chronic inflammation. Ultimately, autologous lymphocytes labelled in accord with the present method could be used for in vivo lymphocyte tracking and clinical imaging of lymphatic malignancies. The present compounds may replace $^{111}$In-oxine as the preferred agent with which to label cultured lymphocytes for imaging metastatic melanoma prior to adoptive immunotherapy.

DETAILED DESCRIPTION OF THE INVENTION

Figure 1:
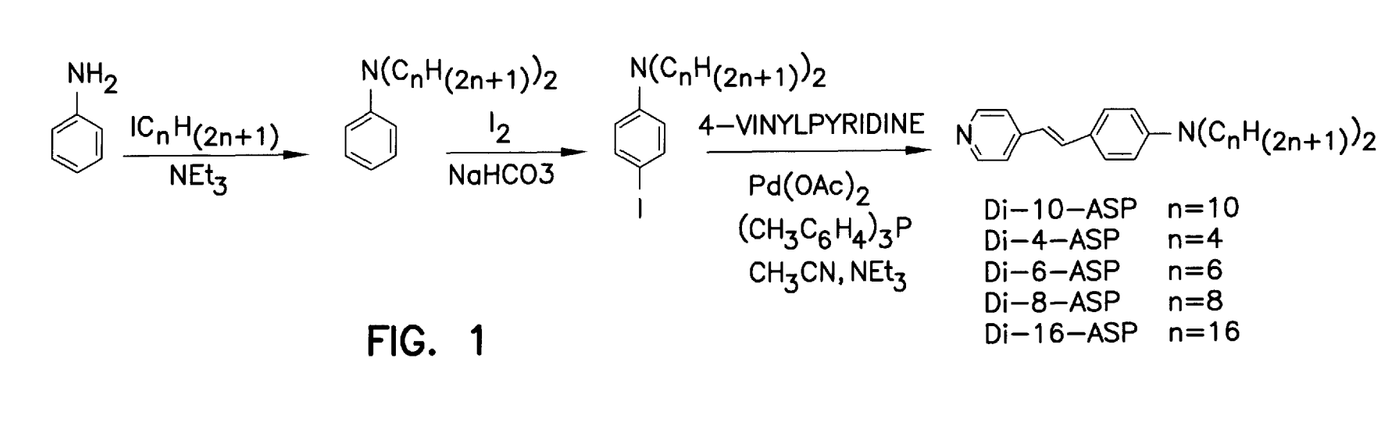
FIG. 1 is a schematic of the synthesis of (dialkylamino)styrylpyridines.

To prepare compounds of formula (I), wherein Det is I—CH=CH—CH$_2$—, the (dialkylamino)styrylpyridines, designated Di—X—ASP wherein X is the length of the alkyl chain, can be synthesized from an aminobenzene as shown in FIG. 1, by the general method of A. Hassner et al., *J. Org. Chem.*, 49, 2546 (1984).

Det is an organic group bound to, or which can bind to, or chelate a radioisotope. The radioisotope can be covalently bound to the organic group, as when Det is CH$_2$CH=CH—X and X is radioactive iodine, or Det can comprise a metal chelating functionality, optionally chelated to a metallic radioisotope.

Preferred among these chelating compounds or "chelators" are such molecules as EDTA, DTPA or DCTA or analogs or homologs thereof, or the compound of the formula:

This formula depicts a cyclohexane-based metal chelator which may be attached to the pyridinium ring N through positions 4 or 5, or through alkyl group R$^3$ and which carries from 1 to 4 metal or nonmetal cations, monovalent cations, or the alkaline earth metals. Thus, with metals of oxidation state +1, each individual cyclohexane-based molecule may carry up to 4 metal cations (where both R$^3$ groups are CH$_2$COOM). As is more likely, with higher oxidation states, the number of metals will decrease to 2 or even 1 per cyclohexane skeleton. The cyclohexane functionality admits of varying stereochemistry, and the aforementioned formula is not intended to limit the molecule to any specific stereochemistry. In particular, both amino functionalities may be either cis or trans to each other.

Preferred cyclohexane ring-containing chelators are of the formula:

and wherein R$^3$ is (C$_1$–C$_4$)alkyl or CH$_2$CO$_2^-$ and M is one equivalent of a cationic metallic radioisotope, such as $^{111}$In or [99m]Tc.

The cyclohexane may be unsubstituted (except for the two nitrogen functionalities) or may be substituted, especially at the 4-position, with a hydroxy or acylated hydroxy group, such as with a lower acyl substitution.

For purposes of this invention, other cyclohexane-based analogs such as alkyl derivatives (e.g., lower alkyl) or substitution products, wherein the derivatization or substitution do not interfere with the linking of the cyclohexane skeleton to N, with the chelating ability (affinity, geometry, etc.) of the individual chelating moieties, are equivalent to those actually shown. Substitutions which are equivalent for the purposes of this invention are hydroxy, acyl, halogen, amino, and the like.

Any metal capable of being detected in a diagnostic procedure in vivo or in vitro can be employed as M in the Det moieties. Particularly, any radioactive metal ion capable of producing a diagnostic result in a human or animal body or in an in vitro diagnostic assay may be used in the practice of the present invention. Suitable ions include the following: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Erbium-169, Europium-152, Gadolinium-153, Gold-195, Gold-199, Hafnium-175, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

Autologous human lymphocytes can be labeled for in vivo tracking and for imaging lymph nodes in normal humans, for imaging lymphatic malignancies, for imaging tumor-involved lymph nodes and staging Hodgkin's disease, for imaging sites of chronic inflammation, and for the diagnosis of acute kidney-graft rejection. Cultured lymphocytes labeled with the present compounds, including interleukin-2 (IL-2) activated autologous peripheral blood lymphocytes (PBLs), tumor-activated killer lymphocytes (TAKs), lymphokine-activated killer cells (LAKs), and tumor infiltrating lymphocytes (TILs) can be used to image tumors.

Lymphocytes are extremely sensitive to radiation damage, and radiotoxicity resulting from nuclear accumulation of $^{111}$In results in decreased lymphocyte proliferative capacity and severe chromosomal aberration. It is well documented that radiotoxicity generally decreases as the distance of a nuclide from the cell nucleus increases. According to various studies, radiation damage from Auger-electron emitters such as $^{111}$In can be reduced 85-fold if the nuclide is confined to the cytoplasm rather than the nucleus, and reduced 120-fold if the nuclide is restricted to the cell membrane. Thus, the present compounds are expected to be particularly useful to label lymphocytes, as they are membrane-restricted.

Figure 2:
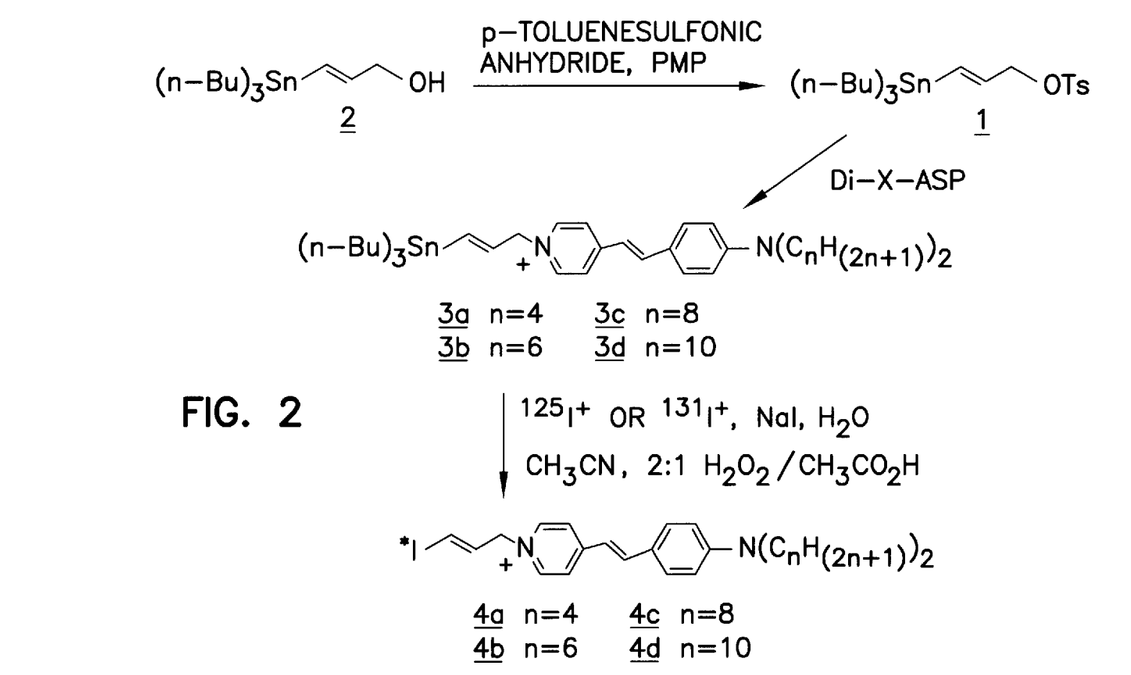
FIG. 2 is a schematic of the synthesis of radioiodinated (dialkylamino)styrylpyridines.

Alkylation of Di-X-ASP with E-1-tributylstannyl-3-tosylpropane (1), prepared by tosylation of the known 1-tributylstannyl-1-propen-3-01 (2) (M. E. Jung et al., Tet. Lett., 32, 3851 (1982)) gave compounds 3a–d (FIG. 2). Reacting 3a–d with $^{125}$I or $^{131}$I, with or without carrier iodide, in acetonitrile/water containing 1–10 µL 2/1 30% hydrogen peroxide/glacial acetic acid for 10 minutes followed by HPLC purification (Spherisorb phenyl column, 6 mM sodium acetate in methanol) gave pure 4a–d. Yields of radioiodinated 4a–d ranged from 47–80% for carrier-added reactions giving specific activities from 250 Ci/mmol to 12000 Ci/mmol. Compound 4d was prepared in theoretical specific activity in a 50% yield with NCA $^{125}$I.

Labeling of mixed leukocytes (harvested from 20 mL canine blood) with 4a–d was performed using five different procedures: 1) labeling in Diluent C (a commercial non-ionic cell labeling media developed by Zynaxis Co. that is not approved for human use) after two saline washes of the cell pellet; 2) labeling in saline after two saline washes of the cell pellet; 3) labeling in saline with no saline washes of the cell pellet; 4 and 5) labeling in ether 10% or 100% platelet poor plasma (PPP). Leukocyte labeling results are summarized in Table 1. Compounds 4a and 4b labeled leukocytes in high yield using either Diluent C, or saline with or without washes of the cell pellet. The introduction of plasma into the labeling media reduced labeling yields. Longer chain compounds 4c and 4d only labeled leukocytes in useful yields using Diluent C.

TABLE 1

Mixed Leukocyte Labeling Yields Using $^{125}$I Labeled ASP Dyes da–d[a,b,c]

| Method | 4a | 4b | 4c | 4d |
|---|---|---|---|---|
| Diluent C | 75% | 75% | 52% | 55% |
|  | (70–79%) | (68–81%) | (37–67%) |  |
| Saline, 2 washes of pellet | 72% | 84% | 32% | 10% |
|  | (71–74%) | (79–87%) | (27–38%) | (8–13%) |
| Saline, no washes of pellet | 71% | 63% | 6% | 2% |
|  | (58–83%) | (42–80%) | (3–9%) | (1–4%) |
| 10% PPP in saline | 41% | 45% | — | — |
|  |  | (28–65%) |  |  |
| 100% PPP | — | 17% | — | — |

[a]10–30 µCi $^{125}$I labeled 4a–d per experiment.
[b]Specific activity ranged from 250–325 Ci/mmol.
[c]Data expressed as the average, range presented in parenthesis.

Peripheral blood lymphocytes (PBLs) from dogs and rats as well as rat splenic lymphocytes were labeled in high yields with either 4a or 4b (Table 2). Viability of labeled lymphocytes was >90% both before and after radiolabeling (Trypan Blue exclusion test).

TABLE 2

Lymphocyte Labeling Yields Using $^{125}$I Labeled ASP Dyes 4a and 4b[a,b,c]

| Animal | Source of Lymphocytes | Separation Procedure | # of cells (× 1,000,000) | Labeling Medium | 4a | 4b |
|---|---|---|---|---|---|---|
| Dog | Blood | Isolymph | 100 | Diluent C | — | 82%[d] |
|  |  |  |  |  |  | (77–85%) |
| Rat | Blood | Histopaque-1077 | 6–44 | PBS | — | 61% |
|  |  |  |  |  |  | (43–75%) |
| Rat | Blood | Isolymph | 15 | PBS | — | 78%[d] |
| Rat | Spleen | Lympholyte-Rat | 63–300 | PBS | 71%[d] | 72%[d] |
|  |  |  |  |  | (62–76%) | (64–77%) |

[a]10–15 µCi $^{125}$I labeled 4a or 4b per experiment.
[b]Specific activity ranged from 200–300 Ci/mmol.
[c]Data expressed as average, range given in parentheses.
[d]Cell viability >90% before and after labeling (Trypan Blue).

Mixed leukocytes labeled with 4b and $^{111}$In-oxine labeled mixed leukocytes were compared in dogs having a sodium urate-induced inflammation in the left stifle joint. Selected results are summarized in Table 3.

TABLE 3

Comparison of $^{125}$I or $^{131}$I-4b Labeled Leukocytes with $^{111}$In-oxine Labeled Leukocytes in Dogs Having a Sodium Urate Induced Abscess in the Stifle Joint

| Experiment No. | Radiopharm. | Labeling Yield | Amount Injected | % inj. dose in abscess aspirate | $^{131}$I/$^{111}$In or $^{125}$I/$^{111}$In in aspirate | % aspirate radioactivity cell bound |
|---|---|---|---|---|---|---|
| 1 | $^{125}$I-4b[a,d] | 84% | 84 µCi | 0.594% | 1.65 | 98% |
|   | $^{111}$In-oxine | 88% | 500 µCi | 0.383% |  | 95% |
| 2 | $^{125}$I-4b[a,c] | 88% | 66 µCi | 0.527% | 6.0 | 96% |
|   | $^{111}$In-oxine | 91% | 312 µCi | 0.088% |  | 98% |
| 3 | $^{131}$I-4b[b,d] | 88% | 88 µCi | 0.050% | 2.6 | 93% |
|   | $^{111}$In-oxine | 85% | 331 µCi | 0.019% |  | 79% |
| 4 | $^{131}$I-4b[c,d] | 88% | 255 µCi | 0.194% | 3.5 | 97% |
|   | $^{111}$In-oxine | 94% | 288 µCi | 0.056% |  | 88% |
| 5 | $^{131}$I-4b[e,f] | 86% | 272 µCi | 0.092% | 4.3 | 95% |
|   | $^{111}$In-oxine | 89% | 326 µCi | 0.021% |  | 92% |
| 6 | $^{131}$I-4b[e,f] | 87% | 211 µCi | 0.355% | 22 | 94% |
|   | $^{111}$In-oxine | 87% | 378 µCi | 0.016% | 22 | 78% |

[a]Specific activity = 250 Ci/mmol
[b]Specific activity = 500 Ci/mmol
[c]Specific activity = 1000 Ci/mmol
[d]Labeling done in Diluent C after cell pellet washed with 2 × 10 mL saline
[e]Specific activity = 800 Ci/mmol
[f]Labeling done in saline after cell pellet washed with 2 × 10 mL saline Gamma camera images of the neck, chest, abdomen, pelvis, right and left legs were obtained at 15 minutes, 1 hour, 2 hours, and 3 hours for Experiment 3 and at 3 hours, 24 hours, and 48 hours for Experiment 4. No lung sequestration was observed with $^{131}$I-4b labeled leukocytes at 15 minutes indicating that 4b and the labeling procedures do not activate leukocytes. At early time points (between 1 hour and 3 hours) images obtained with both the 4b and $^{111}$In-oxine were comparable, and with either radiopharmaceutical the abscess was visible at 3 hours.

In Experiment 3, the 3 hour abscess to contralateral knee and abscess to surrounding tissue ratios were 3.7 and 2.3 for $^{131}$I-4b and 2.7 and 2.0 for $^{111}$In-oxine. At 48 hours (Experiment 4), the abscess to contralateral knee ratio were 9.1 for $^{131}$I-4b and 4.0 for $^{111}$In-oxine while the abscess to surrounding tissue ratio was 6.3 for $^{131}$I-4b and 2.6 for $^{111}$In-oxine. The 48 hour percent injected dose per organ estimated from region of interest (ROI) measurements for the liver and abscess were 8.7% and 1.15% for $^{131}$I-4b and 13.1% for $^{111}$In-oxine.

The effects of a reduced volume of plasma on the cell labeling yield in saline were determined by evaluating the labeling with $^{125}$I-4b, (in 1.5 ml saline) of mixed leukocytes, whose prelabeling cell pellets were washed with either 2×10 mL saline or 1×10 mL saline or not washed. Unwashed mixed leukocytes in 1.5 mL 10% PPP in saline were also tested. Labeling yields were 82%, 84%, 80%, and 83%, respectively. No evidence was found that residual plasma in unwashed cells reduced the labeling yield. Although 10% PPP reduced the yield somewhat, labeling yields are high enough to make this method practical. This ability to label leukocytes in the presence of as little as 10% plasma protects cells from premature activation and damage.

Using $^{125}$I-4b and $^{131}$I-4b, mononuclear leukocytes harvested from 20 mL canine blood via the isolymph method (sodium diatrizoste and Ficol 400, d=1.077) were labeled in 77% and 85% yields, respectively. Thus, the present compounds can label both lymphocytes and mixed leukocytes in high yields, and that the latter can be used to image sites of focal inflammation. The higher localization of leukocytes labeled with $^{131}$I-4b compared to $^{111}$In-oxine in induced inflammatory sites is significant, since $^{111}$In-oxine gives the highest absolute inflammatory lesion uptake of all agents yet tested.

The increased localization observed with the present compounds may be due to an increase in cell viability. Since it has been suggested that the lymphocyte component of labeled mixed leukocytes increases the sensitivity of these mixtures for detecting chronic infections over the sensitivity obtained with pure granulocytes, this improved localization may also be due to an increased contribution by labeled lymphocytes spared the radiation damage they would receive from $^{111}$In-oxine. Thus, the present compounds may be appropriate for tagging lymphocytes in in vivo tracking studies. These results also suggest that mixed leukocytes labeled with the present compounds may image chronic infectious foci with low neutrophilic exudation better than other agents.

Synthesis of Bifunctional Chelating Agents for Preparing $^{111}$In-coordinated Membrane Permeant ASP Compounds

Two routes by which to attach bifunctional chelating agents (BCAs) for $^{111}$In to ASP dyes, were developed. Alkylation of Di-10-ASP with 3-bromopropylisothiocyanate gave 10, which allows attachment of BCAs containing a free amine group. Cyclohexyl EDTA (CDTA) ligand was used to prepare a $^{111}$In-binding BCA with a free amine or with an alkylating group for direct addition to Di-10-ASP. CDTA makes it possible to monofunctionalize (i.e., add a linking group to a single carboxylate of) the ligand. See, R. C. Mease et al., U.S. Pat. No. 5,021,571.

Figure 3:
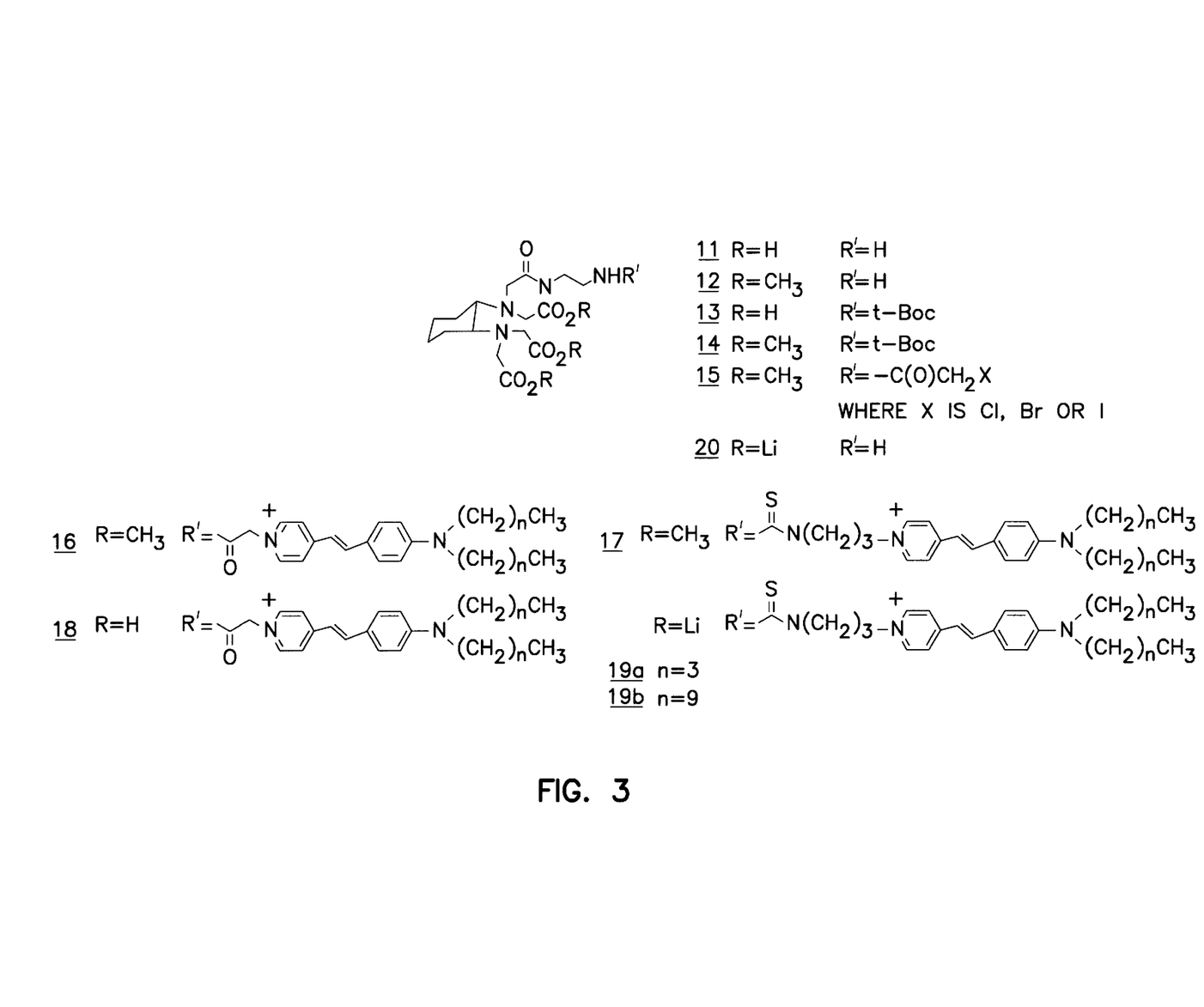
FIG. 3 is a schematic of cyclohexane-based chelators.

Triester 12, shown in FIG. 3, was made by two routes. In the first, ethylenediamine was converted to the mono-t-Boc derivative and reacted with CDTAMA to give 13 (FIG. 3). Methyl iodide esterification gave 14 and was followed by selective hydrolysis to 12 (overall yield 15%). Compound 11 was also converted to 12 by refluxing the ammonium salt of 11 in a solution of methanol, chloroform, and sulfuric acid over 3A molecular sieves (50% yield). Compound 12 reacted with the NHS ester of several α-haloacetic acids to give 15. Reaction of 15 (X=I) with Di-10-ASP, and 11 with 10 gave Di-10-ASP-CDTA conjugates 16 and 17, where the metal-binding carboxylates are masked as esters. A one pot base hydrolysis of 16 (n=5) followed by neutralization and labeling with $^{111}$In gave the $^{111}$In complex of 18 (n=5) in a 68% yield. Alternately, the hydrolysis step was eliminated by preparing 19a (n=3) and 19b (n=9) by reacting the trilithium salt of 11 (compound 20) with compound 10 where n=3 and n=9 respectively. Compound 20 was prepared by the method of Mease et al. U.S. Pat. No. 5,089,663. Indium-111 complexes of compounds 19a and 19b were prepared in an acetate buffer pH 5.5/methanol mixture and purified by HPLC in yields of 55 and 54%. Mixed leukocytes were labeled with [111]In-18 (n=5), [111]In-19a (n=3), and [111]In-19b (n=9) in Diluent C in yields of 21, 4 and 84%, respectively.

The invention will be further described by reference to the following detailed examples.

EXAMPLE 1

Synthesis of 4-[2-[4-(N,N-dibutylamino)phenyl]ethenyl]pyridine (Di-4-ASP);

Preparation of 4-[2-[4-(N,N-dihexylamino)phenyl]ethenyl]pyridine (Di-6-ASP);

Preparation of 4-[2-[4-(N,N-dioctylamino)phenyl]ethenyl]pyridine (Di-8-ASP);

Preparation of 4-[2-[4-(N,N-didecylamino)phenyl]ethenyl]pyridine (Di-10-ASP)

These compounds were prepared following the procedure of A. Hassner et al., *J. Org. Chem.*, 49, 2546 (1984). $^1$H NMR data (300 MHZ, CDCl$_3$) for these compounds is listed below.

Di-10-ASP: H$_a$ δ8.48 (d, J=5.4 Hz, 2H); H$_b$ δ7.27 (d, J=5.4 Hz, 2H); H$_c$ δ6.58 (d,J=7.2 Hz, 2H); H$_d$ δ7.37 (d, J=7.2 Hz, 2H); H$_e$ or H$_f$ δ7.18 (d, J=15.8 Hz, 1H); H$_e$ or H$_f$ δ6.72 (d, J=15.8 Hz, 1H); H$_g$ δ3.28 (app.t, J=7.1 Hz, 4H); H$_h$ δ1.58 (br s, 4H); H$_i$ δ0.88 (app.t, J=7.1 Hz, 6H); H$_j$ δ1.27 (br s, 28H).

Di-8-ASP: H$_a$ δ8.48 (d, 2H); H$_b$ δ7.27 (d, 2H); H$_c$ δ6.58 (d, 2H); H$_d$ δ7.37 (d, 2H); H$_e$ or H$_f$ δ7.18 (d, 1H); H$_e$ or H$_f$ δ6.72 (d, 1H); H$_g$ δ3.28 (app.t, 4H); H$_h$ δ1.58 (br s, 4H); H$_i$ δ0.88 (app.t, 6H); H$_j$ δ1.27 (br s, 20H).

Di-6-ASP: H$_a$ δ8.48 (d, 2H); H$_b$ δ7.27 (d, 2H); H$_c$ δ6.58 (d, 2H); H$_d$ δ7.37 (d, 2H); H$_e$ or H$_f$ δ7.18 (d, 1H); H$_e$ or H$_f$ δ6.72 (d, 1H); H$_g$ δ3.28 (app.t, 4H); H$_h$ δ1.58 (br s, 4H); H$_i$ δ0.88 (app.t, 6H); H$_j$ δ1.27 (br s, 12H).

Di-4-ASP: H$_a$ δ8.48 (d, 2H); H$_b$ δ7.27 (d, 2H); H$_c$ δ6.58 (d, 2H); H$_d$ δ7.37 (d, 2H); H$_e$ or H$_f$ δ7.18 (d, 1H); H$_e$ or H$_f$ δ6.72 (d, 1H); H$_g$ δ3.26 (app.t, 4H); H$_h$ δ1.55 (br m, 4H); H$_i$ δ0.95 (app.t, 6H); H$_j$ δ1.33 (br m, 4H).

EXAMPLE 2

Synthesis of E-1-tributylstannyl-1-propene-3-p-toluenesulfonate (1)

E-1-tributylstannyl-1-propene-3-ol was prepared by the procedure of M. E. Jung et al., *Tet. Lett.*, 23, 3851 (1982). In a dry flask under nitrogen atmosphere, 0.500 g (1.44 mmol) of this material was dissolved in dry 1,2-dichloroethane, and 0.33 g (2.16 mmol) of 1,2,2,6,6-pentamethylpiperidine was added. p-Toluenesulfonic anhydride (0.565 g, 1.73 mmol) was added and the reaction stirred at 50° C. overnight. At the end of this time, solvent was removed under reduced pressure and the crude product redissolved in methylene chloride. Heptane was added and the volume reduced to give a white precipitate of pentamethylpiperidinium tosylate. This solid was filtered and solvent was then removed under reduced pressure from the solution containing E-1-tributylstannyl-1-propene-3-p-toluenesulfonate. The product was chromatographed on silica gel with 5% ethyl acetate/hexane to give 0.6321 g (1.24 mmol, 86% yield) of product.

$^1$H NMR (300 MHz, CDCl$_3$) H$_a$ δ6.27 (dt, J=19.5,1.5 Hz, 1H); H$_b$ δ5.88 (dt, J=19.5,5.4 Hz, 1H); H$_c$ δ4.52 (dd, J=5.4,1.5 Hz, 2H); H$_d$ δ7.79 (d, J=7.9 Hz, 2H); H$_e$ δ7.32 (d, J=7.9 Hz, 2H); H$_f$ (s, 3H); δ1.43, δ1.27, δ0.86 (m, butyl-Sn, 27H).

Elemental analysis: Calculated for C$_{22}$H$_{38}$SO$_3$Sn, C 52.71%, H 7.64%, S 6.40%; Found C 52.83%, H 7.59%, S 6.47%.

EXAMPLE 3

Synthesis of 3-[4-[2-[4-(N,N-didecylamino)phenyl]ethenyl]pyridino]-E-1-tributylstannyl-propene (3d) (Bu$_3$Sn-Di-10-ASP)

In a dry flask under nitrogen atmosphere, Di-10-ASP (0.750 g, 1.57 mmol) was dissolved in 5 mL of 1,2-dichlorobenzene to give an amber solution. E-1-Tributylstannyl-1-propene-3-p-toluenesulfonate (0.867 g, 1.73 mmol) was added to the solution and the reaction was heated 2 days to give a deep red solution. Solvent was removed under reduced pressure at as low a temperature as possible to give the crude product as a thick red oil. The yield of the reaction was estimated by NMR to be at least 80%. The crude material was purified by HPLC prior to radioiodination.

EXAMPLE 4

Synthesis of 3-[4-[2-[4-(N,N-dibutylamino)phenyl]ethenyl]pyridino]-E-1-tributylstannyl-propene (3a) (Bu3Sn-Di-4-ASP); Preparation of 3-[4-[2-[4-(N,N-dihexylamino)phenyl]ethenyl]pyridino]-E-1-tributylstannyl-propene (3b) (Bu3Sn-Di-6-ASP); Preparation of 3-[4-[2-[4-(N,N-dioctylamino)phenyl]ethenyl]pyridino]-E-1-tributylstannyl-propene (3c) (Bu3Sn-Di-8-ASP)

These compounds were made and purified by the procedure described above for Bu$_3$Sn-Di-10-ASP. $^1$H NMR data (300 MHz, CDCl$_3$) of the crude compounds is listed below.

Bu3Sn-Di-10-ASP: Ha δ8.56 (d, J=6.8Hz, 2H); Hb δ7.77 (d, J=6.8Hz, 2H); Hc δ6.57 (d, J=7.7 Hz, 2H); Hd δ7.44 (d, J=7.7 Hz, 2H); He or Hf δ7.49 (d, J=15.8 Hz, 1H); He or Hf δ6.71 (d, J=15.8 Hz, 1H); Hg δ3.27 (app.t, J=7.1 Hz, 4H);

Hh,Hi,Hj, butyl-Sn δ1.58, δ1.43, δ1.26, δ.0.84 (br m integrates higher than theoretical 65H); Hk δ6.25 (m, 1H); Hl δ5.97 (m, 1H); Hm δ5.00 (d, J=7.0 Hz, 2H).

Bu3Sn-Di-8-ASP: Ha δ8.53 (d, 2H); Hb δ7.75 (d, 2H); Hc δ6.60 (d, 2H); Hd δ7.45 (d, 2H); He or Hf δ7.56 (d, 1H); He or Hf δ6.76 (d, 1H); Hg δ3.32 (app.t, 4H); Hh,Hi,Hj, butyl-Sn δ1.58, δ1.43, δ1.26, δ.0.84 (br m integrates higher than theoretical 57H); Hk δ6.28 (m, 1H); Hl δ6.03 (m, 1H); Hm δ5.09 (d, Bu3Sn-Di-6-ASP: Ha δ8.60 (d, 2H); Hb δ7.77 (d, 2H); Hc δ6.60 (d, 2H); Hd δ7.45 (d, 2H); He or Hf δ7.55 (d, 1H); He or Hf δ6.75 (d, 1H); Hg δ3.30 (app.t, 4H); Hh,Hi,Hj, butyl-Sn δ1.58, δ1.43, δ1.26, δ.0.84 (br m integrates higher than theoretical 57H); Hk δ6.30 (m, 1H); Hl δ6.06 (m, 1H); Hm δ5.15 (d, 2H).

Bu3Sn-Di-4-ASP: Ha δ8.50 (d, 2H); Hb δ7.76 (d, 2H); Hc δ6.60 (d, 2H); Hd δ7.44 (d, 2H); He or Hf δ7.55 (d, 1H); He or Hf δ6.75 (d, 1H); Hg δ3.32 (app.t, 4H); Hh,Hi,Hj, butyl-Sn δ1.58, δ1.43, δ1.26, δ.0.84 (br m integrates higher than theoretical 41H); Hk δ6.31 (m, 1H); Hl δ6.05 (m, 1H); Hm δ5.04 (d, 2H).

EXAMPLE 5

Synthesis of 3-[4-[2-[4-(N,N-didecylamino)phenyl]ethenyl]pyridino]-E-1-iodo-propene (I-Di-10-ASP)

Nonradioactive I-Di-10-ASP was prepared directly from Di-10-ASP by an alternative procedure and used as a standard against which to compare the physical properties of radioiodinated I-Di-10-ASP prepared from Bu$_3$Sn-Di-10-ASP. Nonradioactive I-Di-10-ASP was characterized by NMR and the identification was confirmed by accurate mass mass spectral analysis.

$^1$H NMR data (300 MHz, CDCl$_3$) Ha δ8.74 (d, J=5.4 Hz, 2H); Hb δ7.62 (d, J=5.4 Hz, 2H); Hd+He or Hf δ7.53–7.34 (m, 3H); Hk or Hl δ6.96 (d, J=14.7 Hz, 1H); Hc+He or Hf+Hk or Hl δ6.75–6.50 (m, 4H); Hm δ5.13 (d, J=7.1 Hz, 2H); Hg δ3.28 (app.t, J=7.1 Hz, 4H); Hh δ1.58 (br s, 4H); Hi δ0.84 (app.t, J=7.1 Hz, 6H); Hj δ1.24 (br s, 28H).

High resolution mass spectrometry was performed on a Finnigan MAT 95 high resolution mass spectrometer using a Cesium gun for Liquid SIMS (Secondary Ion Mass Spectrometry). Accurate mass analysis of nonradioactive I-Di-10-ASP suggested an empirical formula of C36H56IN2 with a deviation of 0.8 mmu for the cationic portion of the molecule. This is in agreement with the proposed structure.

EXAMPLE 6

Synthesis of N-[methyl(2-(iodoacetamido)ethyl)carbamide]-trans-1,2-diaminocyclohexane N,N', N'-triacetic acid-trimethyl ester N-[methyl(2-(iodoacetamido)ethyl)carbamide]-trans-1,2-diaminocyclohexane N,N',N'-triacetic acid was prepared from cyclohexyl EDTA monoanhydride (R. C. Mease et al., U.S. Pat. No. 5,021,571) and ethylene diamine in a 94% yield as previously reported (R. C. Mease et al., U.S. Pat. No. 5,334,729). This amine was converted to its hydrochloride salt by dissolving it in 100 mL 3M HCl, stirring for 1 h, then concentrating it to a sticky solid. This solid was dried by the addition of 100 mL methanol followed by evaporation under reduced pressure to dryness. This drying procedure was repeated three more times. The resulting powder was placed in a 500 mL round bottom flask to which was added 200 mL methanol, 150 mL methylene chloride, and 9 mL concentrated H$_2$SO$_4$. The flask was equiped with a soxhlet filled with molecular sieves 3A and a reflux condenser. The mixture was refluxed for 10 days, cooled and concentrated to a thick oil. This oil was dissolved in 50 mL CH$_2$Cl$_2$ and added dropwise to a stirred mixture of 200 mL CH$_2$Cl$_2$ and 200 mL saturated NaHCO$_3$ solution. Upon completion of the addition the CH$_2$Cl$_2$ layer was separated and the aqueous layer was extracted with 200 mL CH$_2$Cl$_2$. The methylene chloride portions were combined, dried over MgSO$_4$, and concentrated to give 7.3 g (65% yield) of N-[methyl(2-aminoethyl)carbamide]-trans-1,2-diaminocyclohexane N,N',N'-triacetic acid-triethyl ester.

$^1$H NMR (300 MHz, CDCl$_3$) Ha (δ1.15, m broad, 4H); Hb (δ1.70, m, 2H); Hc (δ1.95, m 2H); Hd (δ2.50, m, 1H) and Hd (δ2.60, m, 1H); He (δ2.75, m, 2H); Hg (δ2.90, d, 1H) and Hg (δ3.18, d, 1H); Hf (δ3.45, m, 2H); δ3.70–3.40 (m, 15H, CO$_2$CH$_3$, NCH$_2$CO$_2$); δ8.45 (t, 1H, C(O)NH).

N-Succinimidyl-iodoacetate was prepared by the method previously used to make N-succinimdyl-bromoacetate (R. C. Mease et al., U.S. Pat. No. 5,089,663). Iodoacetic acid (2.0 g, 10.8 mmol) was dissolved in 100 mL dry CH$_2$Cl$_2$. To this was added 1.2 g (10.8 mmol) N-hydroxysuccinimide, and 2.2 g (10.8 mmol) dicyclohexylcarbodiimide. This mixture was stirred for three days as room temperature under a nitrogen atmosphere. The by-product, dicyclohexylurea was filtered and the filtrate concentrated to give a yellow solid. This was recrystallized from ethyl acetate to give 2.4 g (79%) of a solid (mp 144–147° C.). $^1$H NMR (300 MHz, CDCl$_3$) δ2.85 (s, 2H), δ3.95 (s, 4H)

N-Succinimidyl-iodoacetate (1.52, 5.4 mmol) was dissolved in 50 mL dry CH$_2$Cl$_2$. To this was added dropwise a solution of 2.1 g (4.9 mmol) N-[methyl(2-aminoethyl)carbamide]-trans-1,2-diaminocyclohexane N,N',N'-triacetic-trimethyl ester in 50 mL dry CH$_2$Cl$_2$ under a nitrogen atmosphere at room temperature. The reaction was stirred overnight then partitioned between 100 mL water and 100 mL CH$_2$Cl$_2$. The CH$_2$Cl$_2$ layer was collected, the aqueous layer extracted with 200 mL CH$_2$Cl$_2$, the organic layers combined, dried over MgSO$_4$, filtered, and concentrated to a thick oil. This oil was purified by column chromatography on silica gel using 15:1 CH$_2$Cl$_2$/methanol as eluate to give a thick oil which solidified to yield 1.52 g (52%) of N-[methyl(2-(iodoacetamido)ethyl)carbamide]-trans-1,2-diaminocyclohexane N,N',N'-triacetic acid-trimethyl ester as a glassy solid.

$^1$H NMR (300 MHz, CDCl$_3$) Ha (δ1.15, m broad, 4H); Hb (δ1.70, M, 2H); Hc (δ1.95, m, 2H); Hd (δ2.50, m, 1H) and Hd (δ2.60, m, 1H); Hg (δ2.90, d, 1H) and Hg (δ3.15, d, 1H); δ3.70–3.30 (m, 21,CO$_2$CH$_3$, NCH$_2$CO$_2$, C(O)NCH$_2$CH$_2$NC(O), NC(O)CH$_2$I).

EXAMPLE 7

Synthesis of N-[methyl(2-(Di-10-ASP-acetamido) ethyl)carbamide]-trans-1,2-diaminocyclohexane-N, N',N'-triacetic acid-trimethyl ester Into a flask under a nitrogen atmosphere was added 20mL dry 1,2-dichlorobenzene, 71.5 mg (0.15 mmol) Di-10-ASP, and 98 mg (0.165) N-[methyl(2-(iodoacetamido)ethyl)-carbamide]-trans-1,2-diaminocyclohexane N,N',N'-tiacetic acid-trimethyl ester. The reaction was stirred and heated to 50° C. under nitrogen for 14 days, then concentrated to dryness under reduced pressure to give a dark red colored thick oil. NMR analysis of the crude material showed about 90% conversion to product.

$^1$H NMR (300 MHz, CDCl$_3$) Ha ($\delta$8.75, d, 2H); Hb ($\delta$7.70, d, 2H); He ($\delta$7.55, d, 1H); Hf ($\delta$6.75, d, 1H); Hc ($\delta$7.45, d, 2H); Hd ($\delta$6.60, d, 2H); Hk($\delta$5.50, q, 2H); $\delta$3.7–3.45 (m, 21H, Hp, Hq, Hr, and CO$_2$CH$_3$; Hg ($\delta$3.30, m, 4H); Ho ($\delta$2.60, m, 2H) Hn ($\delta$1.95, m, 2H); Hm ($\delta$1.70, m, 2H); Hh ($\delta$1.55, m, 4H); Hj ($\delta$1.25, m, 28H); Hl ($\delta$1.10, m, 4H); Hi ($\delta$0.80, m, 6H).

EXAMPLE 8

Radioiodination and cell labeling

A. Preparation of No-carrier-added 3-[4-[2-(N,N-didecylamino)phenyl]ethyenyl]pyridino-E-1-[125I]-iodo-propene Fifty micro liters of a concentrated solution of 3-[4-[2-(N,N-didecylamino)phenyl]ethyenyl]pyridino-E-1-tributylstannyl-propene was injected into an a 10 micron Spherisorb phenyl column (this column must never have been exposed to an oxidant) and eluted with 5 mM sodium acetate in methanol. The UV absorbing fraction that eluted at 10-14 minutes was collected (solution is a bright red color). A 1 mL plastic microcentrifuge tube was charged with 130 ul of HPLC eluate fraction eluting at 10–14 minutes, the methanol evaporated under a stream of nitrogen and the residue reconstituted in 100 ul acetonitrile. To this vial was added 10 ul water, 10 ul of a solution of Na$^{125}$I (30 uCi), and 1 ul of a 2:1 mixture of 30% hydrogen peroxide/glacial acetic acid (200 ul 30% H$_2$O$_2$/100 ul glacial acetic acid). This was mixed with a micro pipet and allow to stand for 10 minutes at room temperature. The reaction was diluted with 200 ul 5 mM sodium acetate in methanol and injected on to another HPLC system equipped with an inline UV detector, a radioactive detector and a 10 micron Spherisorb column. The column was eluted with 5 mM sodium acetate in methanol (1 mL/min.). The radioactive peak that eluted at 22 minutes was collected and this fraction was counted to give 15.9 uCi (53%). No UV peak was observed at this retention time so the specific activity was estimated to be 2170 Ci/mmol. A sample of the product was mixed with authentic cold 3-[4-[2-(N,N-didecylamino)phenyl] ethyenyl]pyridino-E-1-iodo-propene and reinjected on to the HPLC; the radioactive material and the UV material co-eluted confirming the identity of the radioactive product.

EXAMPLE 9

Preparation of carrier-added of 3-[4-[2-(N,N-dihexylamino)phenyl]ethyenyl]pyridino-E-1-[$^{131}$I]-iodo-propene Fifty micro liters of a concentrated solution of 3-[4-[2-(N,N-dihexylamino)phenyl]ethyenyl]pyridino-E-1-tributylstannyl-propene was injected into an a 10 micron Spherisorb phenyl column (this column must never have been exposed to an oxidant) and eluted with 5 mM sodium acetate in methanol. The UV absorbing fraction that eluted at 8–10 minutes was collected (solution is a bright red color). A 1 mL plastic microcentrifuge tube was charged with 100 ul of HPLC eluate fraction eluting at 8–10 minutes, the methanol evaporated under a stream of nitrogen and the residue reconstituted in 100 ul acetonitrile. To this vial was added 10 ul water, 10 ul of a solution of Na$^{131}$I (1.18 mCi), 5 micro liters of a 0.28 mmol solution of nonradioactive sodium iodide (1.4 nanomole) in water, and 10 ul of a 2:1 mixture of 30% hydrogen peroxide/glacial acetic acid (200 ul 30% H$_2$O$_2$/100 ul glacial acetic acid). This was mixed with a micro pipet and allowed to stand for 10 minutes at room temperature. The reaction was diluted with 60 ul 5 mM sodium acetate in methanol and injected on to another HPLC system equipped with an inline UV detector, a radioactive detector, and a 10 micron Spherisorb column. The column was eluted with 5 mM sodium acetate in methanol (1 mL/min.). The radioactive and UV absorbing fraction that eluted at 16 minutes was collected and this fraction was counted to give 858 uCi (73%). From the size of the UV peak, the specific activity was estimated to be 300 Ci/mmol.

EXAMPLE 10

Radiolabeling mixed leukocytes with 3-[4-[2-(N,N-dihexylamino)phenyl]ethyenyl]pyridino-E-1-[$^{131}$I]-iodo-propene A 1 mL microcentrifuge tube was charged with 500 ul (600 uCi) of the HLPC eluate of 3-[4-[2-(N,N-dihexylamino)phenyl]ethyenyl]pyridino-E-1-[$^{131}$I]-iodo-propene. This was evaporated to dryness under vacuum in a speed vac and reconstituted into 30 ul ethanol. Forty milli-liters of canine blood was drawn into a 60 mL syringe containing 6.5 mL acetate-citrate-dextrose solution. To this was added 5.5 mL 2% methyl cellulose in saline. The contents of the syringe were gently mixed by several inversions of the syringe and the syringe placed vertically, needle end up, for 45 minutes to allow the red blood cells to settle. The plasma was drawn off and placed into a 50 mL Falcon tube. The tube was centrifuged at 1100 rpm for 15 minutes to pellet the leukocytes. The plasma was removed and the cells resuspended in 2 mL saline. In a 1 mL plastic micro-centrifuge was placed 0.5 mL saline. To this was added 20 ul (372 uCi) of the ethanolic solution of 3-[4-[2-(N,N-dihexylamino)phenyl]ethyenyl]pyridino-E-1-[$^{131}$I]-iodo-propane and mixed. The solution of 3-[4-[2-(N,N-dihexylamino)phenyl]ethyenyl]pyridino-E-1-[$^{131}$I]-iodo-propene in saline was immediately added to the leukocytes and the cells were place vertically on a Nutator rocking apparatus and rocked gently for 20 minutes at room temperature. The cells were then underlayered with 7.5 mL of platelet poor plasma and centrifuged at 1600 rpm for seven minutes to pellet the cells. The supernatant was removed, the cells resuspended in 10 mL saline, and transferred to a new tube. The supernatant, cells, and labeling tube were counted for radioactivity. The cells were centrifuged again at 1600 rpm for 7 minutes, the supernatant removed, and the cells resuspended. After the second centritugation, 340 uCi (91%) of $^{131}$I was bound to the cells.

EXAMPLE 11

Radiolabeling of rat splenic lymphocytes with 3-[4-[2-(N,N-dihexylamino)phenyl]ethyenyl]pyridino-E-1-[$^{125}$I]-iodo-propene A 400 g Sprague-Dawley rat was sacrificed to remove the spleen (1.133 g). The spleen was perfused with phosphate buffered saline to remove the lymphocytes. The lymphocytes in 10 mL PBS were split into two equal portions and each portion was layered onto 5 mL of Lympholyte-Rat (Cedar Lane Laboratories Limited, Ontario, Canada) in a separate 15 mL centrifuge tube. The tubes were centrifuged at 2700 rpm for 20 minutes at room temperature. The lymphoctyes appeared as a layer at the interface of the saline and Lympholyte-Rat layers. The saline layer was removed and discarded. The lymphocyte containing layer from each tube was removed and transferred to a single 50 mL Falcon tube. To this tube was added 10 mL saline and the tube centrifuged for 7 minutes at 1600 rpm. The supernatant was removed, the cells resuspended in 10 mL saline, and centrifuged at 1600 rpm for 7 minutes. The supernatant was removed and the cells suspended in 1 mL saline. Using a hemocytometer, a total of 5 million lymphocytes were counted. Trypan blue exclusion test showed that 12% of the cells were dead. To these cells was added 20 ul of an ethanolic solution of 3-[4-[2-(N,N-dihexylamino)phenyl] ethyenyl]pyridino-E-1-[$^{125}$I]-iodo-propene (15.6 uCi) dissolved in 500 ul of saline. The cells were place vertically on a Nutator rocking apparatus and rocked gently for 20 minutes at room temperature. The cells were then underlayered with 7.5 mL of saline and centrifuged at 1600 rpm for seven minutes to pellet the cells. The supernatant was removed, the cells resuspended in 10 mL saline, and transferred to a new tube. The supernatant, cells, and labeling tube were counted for radioactivity. The cells were centrifuged again at 1600 rpm for 7 minutes, the supernatant removed, and the cells resuspended. After the second centrifugation, 11.9uCi (77%) of $^{131}$I was bound to the lymphocytes. After labeling, 12% of the cells were dead by the trypan blue exclusion test. Therefore, the labeling did not affect cell survival.

EXAMPLE 12

Synthesis of N-[methyl(2-(Di-4-ASP-propylthiourea)ethyl)carbamide]-trans-1,2-diaminocyclohexane-N,N',N'-triacetic acid trilithium salt In a flask under nitrogen atmosphere, 100 mg (0.21 mmol) 1-[g-(isothiocyanato)propyl]-4-[p-(dibutylamino)styryl] pyridinium bromide and 85.5 mg (0.21 mmol) N-[methyl (2-aminoethyl)carbamide]-trans-1,2-diaminocyclohexane N,N',N'-triacetic acid trilithium salt were dissolved in 15 mL dry DMF. The reaction was heated to 80° C. for 5 days, then concentrated to dryness under reduced pressure to give a thick dark red oil. NMR analysis of the crude material showed greater than 95% conversion to product.

$^{1}$H NMR (300 MHz, CD$_3$OD) H$_a$ (δ8.64, d, 2H); H$_b$ (δ7.93, d, 2H); H$_c$ (δ7.78, d, 1H); H$_f$ (δ7.01, d, 1H); H$_e$ (δ7.56, d, 2H); H$_d$ (δ6.67, d, 2H); H$_k$ (δ4.52, br s, 2H); δ3.83–3.15 (br m, 20H, H$_p$, H$_q$, H$_r$, H$_s$, H$_t$, H$_u$, H$_g$; H$_o$ (δ2.35–2.21, br s, 2H) H$_n$ (δ2.08–1.92, br s, 2H); H$_m$ (δ1.83–1.67, br s, 2H); H$_h$ (δ1.65–1.52, br m, 4H); H$_j$ (δ1.45–1.30, br m, 4H); H$_l$ (δ1.52–1.15, br s, 4H); H$_i$ (δ0.96, t, 6H).

EXAMPLE 13

Preparation of the indium-111 complex of N-[methyl(2-(Di-6-ASP-acetamido)ethyl)carbamide]-trans-1,2-diaminocyclohexane-N,N',N'-triacetic acid N-[methyl(2-(Di-6-ASP-acetamido)ethyl)carbamide]-trans-1,2-diaminocyclohexane-N,N',N'-triacetic acid trimethyl ester was prepared analogously to Example 7. Fifty micro liters of a concentrated solution of the trimethyl ester in dichloromethane was injected onto a 10 micron Spherisorb phenyl column and eluted with 20 mM ammonium acetate in methanol at a flow rate of 1.5 mL/min. The UV absorbing fraction (280 nm) that eluted at 4 min was collected. This fraction is bright red. A 1 mL plastic microcentrifuge tube was charged with 500 μL of the HPLC eluate, and the methanol was evaporated under a stream of nitrogen. To the residue was added 75 μL methanol, 20 μL water, and 10 μL 1M NaOH. The mixture was allowed to stand 20 min before 10 μL 1M HCl was added followed by 50 μL methanol, 15 μL acetate buffer (0.3M sodium acetate and 0.14M acetic acid, pH 5.5) and 100 μL $^{111}$InCl$_3$ in 0.05M HCl (1.26 mCi). The mixture was left to stand 20 min at room temperature. The contents of the tube were then injected onto an HPLC system fitted with in line UV (280 nm) and radioactivity detectors and a Spherisorb phenyl column. The column was eluted with 40 mM sodium acetate in methanol (1.5 mL/min). The radioactive peak eluting at 6min was collected (862 μCi, 68% yield).

EXAMPLE 14

Preparation of the indium-111 complex of N-[methyl(2-(Di-4-ASP-propylthiourea)ethyl) carbamide]-trans-1,2-diaminocyclohexane-N,N',N'-triacetic acid Prior to complexation, the starting material was purified by HPLC. One 100 μL hundred micro liters of a methanol solution of N-[methyl(2-(Di-4ASP-propylthiourea)ethyl) carbamide]-trans-1,2-diaminocyclohexane-N,N',N'-triacetic acid trilithium salt was injected onto a Spherisorb phenyl column (10 micron) and eluted isocratically (1 mL/min) with a mixture of mixture of 5 mM ammonium acetate/methanol (95%) and acetonitrile (5%). The WV absorbing fraction (280 nm) that eluted at 4 min was collected. This fraction appears orange to the naked eye. A 1 mL plastic microcentrifuge tube was charged with 200 μL of the eluate and the solution was evaporated to dryness. The residue was reconstituted in 100 μL methanol, and 100 μL acetate buffer was added (0.3M sodium acetate and 0.14M acetic acid, pH 5.5). Eighty micro liters of a solution composed of 630 µCi $^{111}$InCl$_3$ in 0.05M HCL was added to the microcentrifuge tube, and the reaction was mixed and left to stand 1 h at room temperature. The contents of the tube were then injected onto an HPLC system fitted with in line UV (280 nm) and radioactivity detectors and a Spherisorb phenyl column. The column was eluted with a 95:5 mixture of 10 mM ammonium acetate in methanol and acetonitrile. The radioactive peak eluting at 7 min was collected (342 µCi, 54% yield).

EXAMPLE 15

Radiolabeling mixed leukocytes with the indium-111 complex of N-[methyl(2(Di-10-ASP-propylthiourea)ethyl)carbamide]-trans-1,2-diaminocyclohexane-N,N',N'-triacetic acid Six milliliters of HPLC eluate containing the indium-111 complex of N-[methyl(2-(Di-10-ASP-propylthiourea)ethyl) carbamide]-trans-1,2-diaminocyclohexane-N,N',N'-triacetic acid was evaporated to dryness in a speed vac and reconstituted in 80 µL ethanol. A sample of canine blood (20 mL) was drawn into a 60 mL syringe containing 3 mL acetate-citrate-dextrose (ACD) solution. To this was added 3 mL 2% methyl cellulose in saline. The contents of the syringe were gently mixed by several inversions, and the syringe was then placed vertically, needle end up, for 45 min to allow the red blood cells to settle. The plasma was drawn off and transferred to a 50 mL Falcon tube. The tube was centrifuged at 1100 rpm for 15 min to pellet the leukocytes. The plasma was removed and the cells resuspended in 10 mL saline. The tube was centrifuged at 1600 rpm for 7 min, the supernatant removed, and the cells resuspended in 10 mL saline and recentrifuged at 1600 rpm for 7 min. The supernatant was then removed and the cells resuspended in 2 mL Diluent C. Into a 1 mL plastic microcentrifuge tube was placed 0.5 mL Diluent C. To this was added 20 µL (44.4 µCi) of the ethanolic solution of the $^{111}$In complex of N-[methyl(2-(Di-10-ASP-propylthiourea)ethyl)carbamide]-trans-1,2-diaminocyclohexane-N,N',N'-triacetic acid and mixed. The indium complex in Diluent C was immediately added to the leukocytes and the cells were placed vertically on a Nutator rocking apparatus and rocked gently for 30 min at room temperature. The cells were then underlayered with 5 mL of platelet poor plasma and centrifuged at 1600 rpm for 7 min to pellet the cells. The supernatant was removed, the cells resuspended in 10 mL saline, and transferred to a new tube. The supernatant, cells, and labeling tube were counted for radioactivity. The cells were centrifuged again at 1600 rpm for 7 min, the supernatant removed, and the cells resuspended. After the second centrifugation, 37.4 µCi (84%) $^{111}$In was bound to the cells.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula (I):

wherein Det is an organic group comprising a detectable radioisotope, n is 4–16, and Z$^-$ is a biologically acceptable anion.

2. The compound of claim 1 wherein Det is —CH$_2$—CH=CH—X wherein X is $^{123}$I, $^{125}$I, or $^{131}$I.

3. The compound of claim 1 wherein Det is a chelating group comprising a radioactive metal.

4. The compound of claim 3 wherein the radioactive metal is $^{111}$In or $^{99m}$Tc.

5. The compound of claim 1 wherein Det is:

wherein M is radioactive metal and R$^3$ is (C$_1$–C$_4$)alkyl or CH$_2$CO$_2^-$.

6. The compound of claim 5 wherein M is $^{111}$In or $^{99m}$Tc.

7. The compound of claim 1 wherein n is 6–10.

8. A compound of the formula (II):

wherein n is 4–16 and Z$^-$ is an anion.

9. The compound of claim 8 wherein n is 6–10.

* * * * *

UNITED STATES PATENT AND TRADEMARK OFFICE
CERTIFICATE OF CORRECTION

PATENT NO. : 5,840,859
DATED : November 24, 1998
INVENTOR(S) : Carol Lambert, et al It is certified that error appears in the above-identified patent and that said Letters Patent is hereby corrected as shown below:

In column 1, line 10, after "1995," insert --"This invention was made with Government support under contract No. CA-32853, awarded by the National Institute of Health. The Government has certain rights in the invention"-- therefor.

In column 18, line 41, after "M is," insert --a-- therefor.